United States Patent
Maubru et al.

(10) Patent No.: US 6,475,499 B2
(45) Date of Patent: Nov. 5, 2002

(54) COMPOSITION FOR WASHING KERATIN MATERIALS, BASED ON WEAKLY ETHOXYLATED SORBITAN ESTER

(75) Inventors: Mireille Maubru, Chatou; Sandrine Decoster, Saint-Gratien; Bernard Beauquey, Clichy, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/757,485

(22) Filed: Jan. 11, 2001

(65) Prior Publication Data

US 2001/0009909 A1 Jul. 26, 2001

(30) Foreign Application Priority Data

Jan. 21, 2000 (FR) .............................. 00 00790

(51) Int. Cl.[7] .............................. A61K 7/00; A61K 7/48; A61K 7/50; A61K 7/08
(52) U.S. Cl. ................... 424/401; 424/70.1; 424/70.31
(58) Field of Search .............. 424/401, 70.1, 424/70.31; 510/122, 123

(56) References Cited

U.S. PATENT DOCUMENTS

| 3,819,524 A | 6/1974 | Schubert et al. ............ 252/90 |
| 3,988,255 A | 10/1976 | Seiden ....................... 252/107 |
| 4,772,427 A | 9/1988 | Dawson et al. .............. 252/559 |
| 5,482,705 A | 1/1996 | Hoffmann, Jr. et al. ....... 424/73 |
| 5,650,383 A | * 7/1997 | Dubief et al. ................ 510/122 |
| 5,696,069 A | * 12/1997 | Ito et al. ..................... 510/123 |
| 5,911,981 A | 6/1999 | Dahms et al. ........... 424/70.19 |

FOREIGN PATENT DOCUMENTS

| EP | 0 642 782 | 3/1995 |
| FR | 2 753 373 | 3/1998 |

* cited by examiner

Primary Examiner—Jose' G. Dees
Assistant Examiner—M. Haghighatian
(74) Attorney, Agent, or Firm—Nixon & Vanderhye P.C.

(57) ABSTRACT

The invention relates to compositions for washing keratin materials, comprising, in a cosmetically acceptable medium containing at least one anionic detergent surfactant, at least one oxyethylenated sorbitan ester of a $C_8$–$C_{30}$ fatty acid with a number of moles of ethylene oxide of less than or equal to 10. These compositions have a weight ratio anionic detergent surfactant agent/sorbitan ester of $C_8$–$C_{30}$ fatty acid ranging from 0.5 to 5.

22 Claims, 1 Drawing Sheet

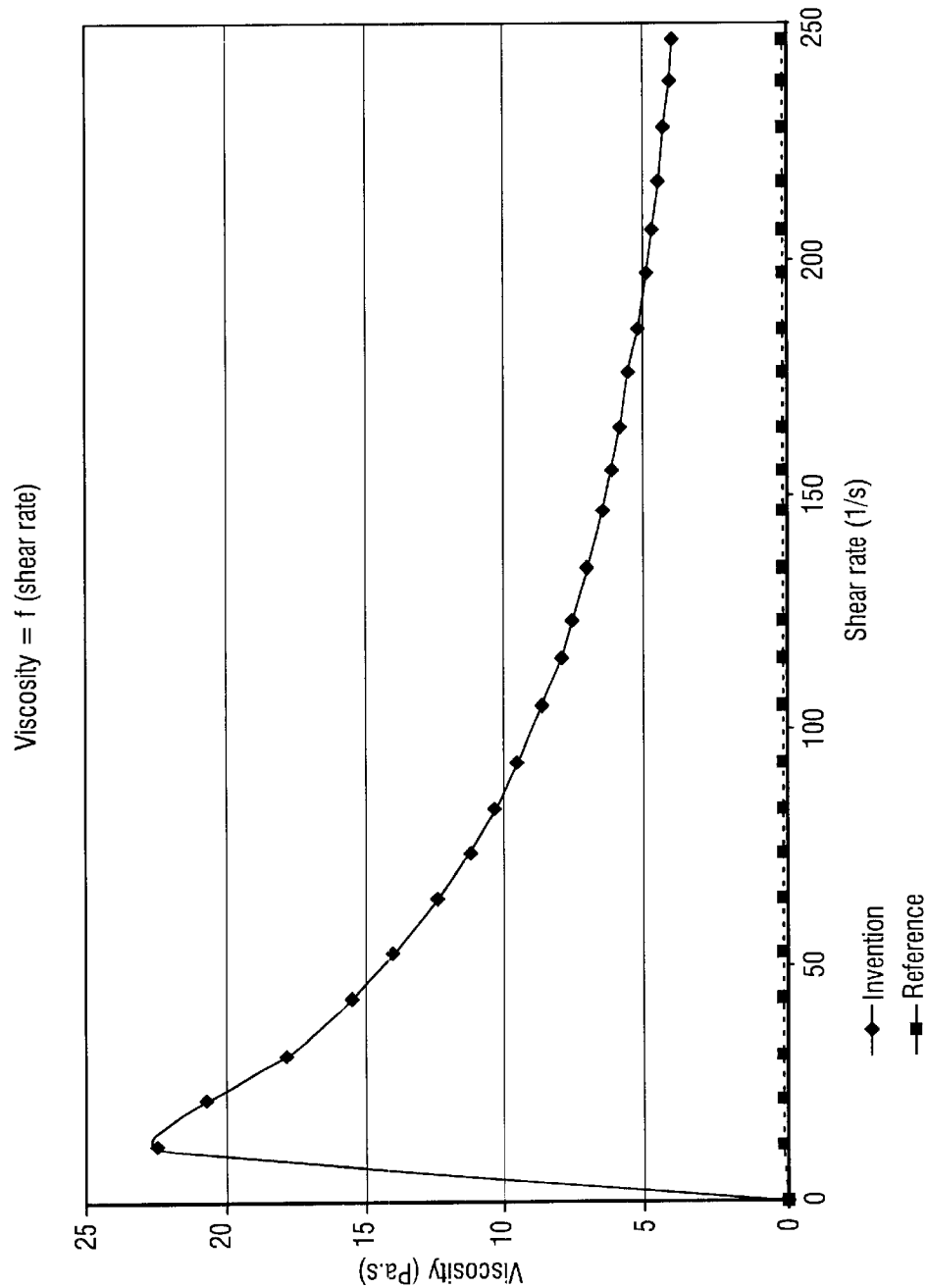

COMPOSITION FOR WASHING KERATIN MATERIALS, BASED ON WEAKLY ETHOXYLATED SORBITAN ESTER

The present invention relates to compositions for washing keratin materials, and in particular the hair and/or the skin, based on weakly ethoxylated sorbitan ester, and to the washing process using these compositions.

It is known practice to use nonionic surfactants such as highly polyoxyethylenated sorbitan esters in shampoos. These sorbitan esters act as auxiliary detergents in this type of formulation.

Belgian patent No. 840 667 (Johnson & Johnson) discloses detergent compositions and shampoos based on combinations of nonionic surfactants such as highly ethoxylated sorbitan esters that are only mildly irritant to the eyes but have satisfactory foaming power. These sorbitan esters comprise about 40 ethylene oxide units, the compound especially preferred comprising 44 ethylene oxide units.

In the said patent, the detergent compositions necessarily contain at least one polyoxyethylenic derivative of a hydrophobic base as nonionic surfactant, an anionic surfactant and a surfactant betaine. It is the combination of these three compounds which gives the composition a foam of satisfactory stability which is only mildly irritant to the eyes.

Similarly, patent application EP 0 815 851 A2 discloses compositions, especially shampoos comprising highly oxyethylenated sorbitan esters, with at least 20 ethylene oxide units, in combination with anionic surfactants in order to reduce the eye irritation in the presence of anionic surfactants.

Patent application EP 0 453 238 A1 discloses cosmetic compositions used in the form of shampoos which impart softness and good foaming capacity. These compositions comprise surfactants of different types and in particular sorbitan esters such as Polysorbate 20 and Polysorbate 80 comprising approximately 20 mol of ethylene oxide. These compositions comprise at least one nonionic surfactant compound in combination with at least one anionic surfactant and one amphoteric surfactant.

All these prior art compositions have the characteristic of being difficult to thicken, which leads to mediocre usage qualities: poor distribution of the product, difficult emulsification, charged feel.

The Applicant has discovered, surprisingly, that it is possible to formulate compositions for washing keratin materials, especially shampoos, which display good eye tolerance and produce improved thickening of shampoo formulations, by using a weakly oxyethylenated sorbitan ester having a number of moles of ethylene oxide of less than or equal to 10. These results are obtained by using in particular a weight ratio anionic detergent surfactant agent/sorbitan ester ranging from 0.5 to 5.

One subject of the invention is compositions for washing keratin materials, comprising at least one anionic detergent surfactant and at least one sorbitan ester having a number of moles of ethylene oxide of less than or equal to 10, in a weight ratio anionic detergent surfactant agent/sorbitan ester ranging from 0.5 to 5.

A subject of the invention is also the use of at least one sorbitan ester having a number of moles of ethylene oxide of less than or equal to 10, with the aim of reducing the eye-irritant potential and of improving the thickening of compositions for washing keratin materials containing a detergent surfactant.

Another subject of the invention is a process for washing keratin materials.

Other subjects of the invention will become apparent on reading the description and the examples which follow.

The compositions for washing keratin materials in accordance with the invention comprise, in a cosmetically acceptable medium containing at least one anionic detergent surfactant, at least one sorbitan ester of a saturated or unsaturated, linear or branched $C_8$–$C_{30}$, preferably $C_8$–$C_{20}$, fatty acid in a weight ratio of the anionic detergent surfactant to the sorbitan ester of $C_8$–$C_{30}$ fatty acid ranging from 0.5 to 5.

Oxyethylenated sorbitan monoesters with a number of moles of ethylene oxide of less than or equal to 10 are preferably used.

The number of moles of ethylene oxide is preferably between 3 and 8 mol of ethylene oxide.

The sorbitan esters that are preferred are oxyethylenated sorbitan monolaurate (4EO) or Polysorbate 21, oxyethylenated sorbitan monostearate (4EO) or polysorbate 61 and oxyethylenated sorbitan monooleate (5EO) or Polysorbate 81.

According to the present invention, the sorbitan ester may be present in the composition for washing keratin materials in proportions of from 0.5% to 20% and preferably from 2% to 15% by weight relative to the total weight of the said composition.

The patent proprietor has discovered that the addition of weakly oxyethylenated sorbitan ester, mentioned above, makes it possible, surprisingly, to reduce the irritant nature, in particular the eye-irritant nature, of washing compositions containing detergent surfactants such as anionic surfactants, in particular alkyl sulphates and alkyl ether sulphates, which are liable to cause irritation when they are used alone.

Among the anionic surfactants which may be mentioned are the alkaline salts, ammonium salts, amine salts, amino alcohol salts and magnesium salts of the following compounds: alkyl sulphates, alkyl ether sulphates, alkylamidoether sulphates, alkylarylpolyether sulphates, monoglyceride sulphates; alkylsulphonates, alkylamide sulphonates, alkylarylsulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates and alkyl ether phosphates; acyl sarcosinates, acyl isethionates and N-acyl taurates.

Among the anionic surfactants which may also be mentioned are fatty acid salts such as oleic, ricinoleic, palmitic and stearic acid salts; coconut oil acid or hydrogenated coconut oil acid; acyl lactylates. The acyl or alkyl radicals generally comprise from 8 to 30 carbon atoms.

It is also possible to use surfactants, such as polyoxyalkylenated alkyl or alkylaryl ether carboxylic acids or salts thereof, polyoxyalkylenated alkylamido ether carboxylic acids or salts thereof, and alkyl D-galactoside uronic acids or salts thereof.

The anionic surfactant is preferably used in proportions of between 1% and 50% by weight and more particularly between 5% and 40% by weight relative to the total weight of the composition.

The composition of the present invention preferably contain no soap.

The composition of the present invention can also contain one or more detergents chosen from nonionic surfactants other than the weakly oxyethylenated sorbitan esters defined above, amphoteric surfactants and zwitterionic surfactants in proportions that are sufficient to give the composition detergent properties.

The additional nonionic surfactants are chosen more particularly from polyethoxylated, polypropoxylated or polyglycerolated fatty acids or alkylphenols or alcohols, with a fatty chain containing 8 to 18 carbon atoms, the number of ethylene oxide or propylene oxide groups being between 2 and 50 and the number of glycerol groups being between 2 and 30, with the exception of oxyethylenated $C_8$–$C_{30}$ fatty acid esters of sorbitan with a number of moles of ethylene oxide of less than or equal to 10.

Mention may also be made of copolymers of ethylene oxide and of propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 glycerol groups and in particular 1.5 to 4; polyethoxylated fatty amines preferably containing 2 to 30 mol of ethylene oxide; fatty acid esters of sorbitan oxyethylenated with 12 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or N-acylamidopropyl-morpholine oxides.

The amphoteric surfactants that are preferred are secondary or tertiary aliphatic amine derivatives, in which the aliphatic radical is a linear or branched chain comprising 8 to 22 carbon atoms and which contains at least one carboxylate, sulphonate, sulphate, phosphate or phosphonate water-solubilizing anionic group; ($C_8$–$C_{20}$) alkylbetaines, sulphobetaines ($C_8$–$C_{20}$) alkylamido ($C_1$–$C_6$) alkylbetaines or ($C_8$–$C_{20}$)alkylamido($C_1$–$C_6$) alkylsulphobetaines.

Among the amine derivatives which may be mentioned are the products sold under the name Miranol, as disclosed in patents U.S. Pat. Nos. 2,528,378 and 2,781,354 and classified in the CTFA dictionary, $7^{th}$ edition, 1997, under the name Disodium Cocoamphodiacetate, Disodium Lauroamphodiacetate, Disodium Capryloamphodiacetate, Disodium Caproamphodiacetate, Disodium Cocoamphodipropionate, Disodium Lauroamphodipropionate, Disodium Caproamphodipropionate, Disodium Capryloamphodipropionate, Lauroamphodipropionate acid, Cocoamphodipropionate acid.

The detergent surfactants are generally present in proportions of between 1% and 50% by weight relative to the total weight of the composition and preferably between 5% and 40% by weight.

According to one preferred embodiment, the compositions in accordance with the invention contain at least one anionic surfactant, at least one weakly oxyethylenated sorbitan ester and at least one amphoteric surfactant.

The compositions can also contain cationic surfactants preferably used in proportions of between 0.001% and 5% by weight relative to the total weight of the composition.

The cationic surfactants are chosen in particular from optionally polyoxyalkylenated primary, secondary and tertiary fatty amine salts; quaternary ammonium salts; imidazoline derivatives; and amine oxides of cationic nature.

The quaternary ammonium salts that are preferred are tetraalkylammonium halides (for example chlorides) such as, for example, dialkyldimethylammonium or alkyltrimethylammonium chlorides, in which the alkyl radical comprises from about 12 to 22 carbon atoms, in particular behenyltrimethylammonium chloride, distearyldimethylammonium chloride, cetyltrimethylammonium chloride, benzyldimethylstearylammonium chloride or stearamidopropyldimethyl(myristyl acetate)ammonium chloride, which are sold under the name "Cepharyl 70" by the company Van Dyk.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (in particular chlorides or methyl sulphate), and mixtures thereof, can also be used.

The acyl radicals are more particularly derived from a plant oil such as palm oil or sunflower oil.

The concentration of additional surfactants other than anionic surfactants can range from 0% to 30% and preferably from 0.5% to 15% by weight relative to the total weight of the composition.

The compositions according to the invention can also contain silicones, that is to say polyorganosiloxane oils, or polyorganosiloxane gums or resins, such as in the form of solutions in organic solvents or alternatively in the form of emulsions or microemulsions.

Among the polyorganosiloxanes which can be used in accordance with the present invention, mention may be made, in a non-limiting manner, of:

volatile silicones: these have a boiling point between 60° C. and 260° C. They are chosen from cyclic silicones containing from 3 to 7 and preferably 4 to 5 silicon atoms;

non-volatile silicones: these consist mainly of polyalkylsiloxanes, polyarylsiloxanes, polyalkylarylsiloxanes, silicone gums and silicone resins or mixtures thereof, and organomodified silicones.

Polydimethylsiloxanes, aminosilicones and oxyalkylenated silicones are used more particularly.

The polyorganosiloxanes may be used in the compositions of the invention in proportions of between 0.01% and 20% by weight and preferably between 0.1% and 10% by weight relative to the total weight of the composition.

The compositions of the invention can also contain a cationic or amphoteric polymer.

The cationic polymers used generally have a number-average molecular mass of between 500 and $5.10^6$ approximately and preferably between $10^3$ and $3.10^6$ approximately.

Among the cationic polymers which may be mentioned are quaternized proteins (or protein hydrolysates) and polymers such as polyamines, polyamino amides and polyquaternary ammoniums. These are known products.

The quaternized proteins or protein hydrolysates are, in particular, chemically modified polypeptides bearing quaternary ammonium groups at the end of a chain or grafted thereon. Their molecular mass can range, for example, from 1500 to 10,000 and particularly from 2000 to 5000 approximately.

The polymers of the polyamine, polyamino amide or polyquaternary ammonium type which can be used in accordance with the present invention and which may be mentioned in particular are those disclosed in French patents No.s 2 505 348 and 2 542 997. Among these polymers, mention may be made of:

(1) Quaternized or non-quaternized vinylpyrrolidone/dialkylaminoalkyl acrylate or methacrylate copolymers, such as the polymers disclosed in detail in French patents 2 077 143 and 2 393 573.

(2) The cellulose ether derivatives comprising quaternary ammonium groups disclosed in French patent 1 492 597.

(3) Cationic cellulose derivatives, such as the copolymers of cellulose or of cellulose derivatives grafted with a water-soluble quaternary ammonium monomer, and disclosed in particular in U.S. Pat. No. 4,131,576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

(4) The polysaccharides and in particular cationic guar gums disclosed more particularly in U.S. Pat. Nos. 3,589,578 and 4,031,307.

(5) Polymers consisting of piperazinyl units and of alkylene or hydroxyalkylene divalent radicals containing straight or branched chains, optionally interrupted with oxygen, sulphur or nitrogen atoms or with aromatic or heterocyclic rings, as well as the oxidation and/or quaternization products of these polymers. Such polymers are disclosed in particular in French patents 2 162 025 and 2 280 361.

(6) The water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or an oligomer resulting from the reaction of a difunctional compound which is reactive with respect to a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyamino amide; these polyamino amides can be alkylated or, if they comprise one or more tertiary amine functions, can be quaternized. Such polymers are disclosed in particular in French patents 2 252 840 and 2 368 508.

(7) The polyamino amide derivatives resulting from the condensation of polyalkylene polyamines with polycarboxylic acids followed by an alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are disclosed in particular in French patent 1 583 363.

(8) The polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, the molar ratio between the polyalkylene polyamine and the dicarboxylic acid being between 0.8:1 and 1.4:1, the resulting polyamino amide being made to react with the epichlorohydrin in a molar ratio of epichlorohydrin relative to the secondary amine group of the polyamino amide of between 0.5:1 and 1.8:1. Such polymers are disclosed in particular in U.S. Pat. Nos. 3,227,615 and 2,961,347.

(9) Copolymers of methyldiallylamine or of dimethyldiallylammonium, in particular those disclosed in French patent 2 080 759 and its certificate of addition 2 190 406.

(10) The diquaternary ammonium polymers disclosed in French patents 2 320 330, 2 270 846, 2 316 271, 2 336 434 and 2 413 907 and in the patents U.S. Pat. Nos. 2,273,780, 2,375,853, 2,388,614, 2,454,547, 3,206, 462, 2,261,002, 2,271,378, 3,874,870, 4,001,432, 3,929,990, 3,966,904, 4,005,193, 4,025,617, 4,025, 627, 4,025,653, 4,026,945 and 4,027,020.

(11) The polyquaternary ammonium polymers disclosed in particular in patent application EP-A-122 324.

(12) Homopolymers or copolymers derived from acrylic or methacrylic acids and comprising units of the type

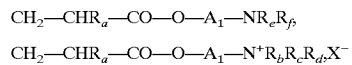

and/or

in which the groups $R_a$ independently denote H or $CH_3$, the groups $A_1$ independently denote a linear or branched alkyl group of 1 to 6 carbon atoms or a hydroxyalkyl group of 1 to 4 carbon atoms, the groups $R_b$, $R_c$, and $R_d$, which may be identical or different, independently denote an alkyl group of 1 to 18 carbon atoms or a benzyl radical, the groups $R_e$ and $R_f$ represent a hydrogen atom or an alkyl group of 1 to 6 carbon atoms, and $X^-$ denotes an anion, for example methosulphate or a halide such as chloride or bromide,

(13) quaternary vinylpyrrolidone and vinylimidazole polymers such as, for example, the products sold under the names "Luviquat FC 905", "Luviquat FC 550" and "Luviquat FC 370" by the company BASF.

(14) Polyamines such as "Polyquart H" sold by Henkel, referred to under the name "Polyethylene glycol tallow polyamine" in the CTFA dictionary.

(15) Crosslinked polymers of methacryloyloxyethyltrimethylammonium salt, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by a crosslinking with a compound containing olefinic unsaturation, in particular methylenebisacrylamide. It is more particularly possible to use an acrylamide/methacryloyloxyethyltrimethylammonium chloride crosslinked copolymer (20/80 by weight) in the form of a dispersion containing 50% by weight of the said copolymer in mineral oil.

Other cationic polymers which can be used in the context of the invention are polyalkyleneimines, in particular polyethyleneimines, polymers . containing vinylpyridine or vinylpyridinium units, condensates of polyamines and of epichlorohydrin, polyquaternary ureylenes and chitin derivatives.

Among all the cationic polymers which can be used in the context of the present invention, the ones that are preferred are cellulose ether derivatives comprising quaternary ammonium groups, polysaccharides, and in particular cationic guar gums, and cyclopolymers of methyldiallylammonium or of dimethyldiallylammonium.

The cationic polymers are used in the compositions of the invention in proportions of between 0.001% and 20% by weight and preferably between 0.05% and 5% by weight relative to the total weight of the composition.

The compositions according to the invention have a pH generally of between 3 and 12 and more particularly between 4 and 8.

The cosmetically acceptable medium for compositions consists either of water or of one or more solvents, or of a mixture of water and of at least one solvent chosen from lower alcohols, alkylene glycols and polyol ethers.

The compositions according to the invention can also contain viscosity regulators, such as electrolytes, for instance sodium chloride, thickeners, for instance cellulose derivatives such as, for example, carboxymethylcellulose, hydroxypropylcellulose or hydroxyethylcellulose, guar gum, hydroxypropyl guar gums, scleroglucans, xanthan gum and amphiphilic polymers comprising at least one fatty chain.

The compositions according to the invention can also contain various adjuvants commonly used in cosmetics, such as fragrances, preserving agents, foam synergists, sequestering agents, foam stabilizers, propellants, dyes, anti-dandruff agents, ceramides, vitamins or provitamins, hydroxy acids, acidifying or basifying agents, plant, mineral or animal oils, synthetic oils such as polyisobutenes and polydecenes, fatty acid esters, pseudoceramides, nacreous agents or other adjuvants depending on the use envisaged.

A subject of the invention is also the use of at least one above-defined sorbitan ester Of $C_8$–$C_{30}$ fatty acid in a shampoo.

Another subject of the present invention is a process for washing keratin materials, which consists in applying at least one composition of the present invention to these materials, followed by rinsing of the treated materials after an optional exposure time.

The examples which follow are intended to illustrate the invention without thereby being limiting in nature.

EXAMPLE 1

The composition below is prepared:

| | |
|---|---|
| Sodium lauryl ether sulphate (70/30 C12/C14) Containing 2.2 mol of ethylene oxide | 7.0 g A.M. |
| Cocoylamidopropylbetaine as an aqueous solution containing 38% A.M. | 3.8 g A.M. |
| Sorbitan monostearate oxyethylenated with 4 mol of ethylene oxide, sold under the name "Tween 61" by Uniqema | 6.0 g |
| Lauryl alcohol oxyethylenated with 2.5 mol of ethylene oxide | 1.0 g |
| Hydroxyethylcellulose crosslinked with epichlorohydrin and quaternized with trimethylamine, sold under the name "JR 400" by the company Union Carbide | 0.2 g |
| Preserving agents | qs |
| Demineralized water | qs 100.0 g pH 7.0 |

EXAMPLE 2

The composition below is prepared:

| | |
|---|---|
| Sodium lauryl ether sulphate (70/30 C12/C14) containing 2.2 mol of ethylene oxide | 8.4 g A.M. |
| Lauryl monosulphosuccinate containing 3 mol of ethylene oxide, disodium salt, as a protected aqueous solution containing 30% A.M. | 2.6 g A.M. |
| Sorbitan monooleate oxyethylenated with 5 mol of ethylene oxide, sold under the name "Tween 81" by Uniqema | 5.0 g |
| Polyethylene glycol (55 mol of ethylene oxide) and propylene glycol dioleate, as an aqueous-glycolic solution, sold under the name "Antil 141 Liquid" by the company Goldschmidt | 5.0 g |
| Hydroxypropyl guar trimethylammonium chloride, sold under the name "Jaguar C162" by the company Rhodia | 0.05 g |
| Sodium hydroxide | qs pH 7.0 |
| Preserving agents | qs |
| Demineralized water | qs 100.0 g |

EXAMPLE 3

The composition below is prepared:

Comparative Examples

The compositions below were prepared:

EXAMPLE 4A: (according to the invention): Composition containing weakly oxyethylenated sorbitan ester nonionic surfactant such as Tween 21 (4 mol of ethylene oxide).

EXAMPLE 4B: Composition containing highly oxyethylenated sorbitan ester nonionic surfactant, such as Tween 20 (20 mol of ethylene oxide).

The thickening of the shampoo formulations is markedly easier when a highly oxyethylenated sorbitan ester such as Tween 20 (20 mol of ethylene oxide), which is conventionally used in shampoos for children, is replaced with a less oxyethylenated compound such as Tween 21 (4 mol of ethylene oxide) and the shampoo obtained moreover has excellent eye tolerance.

EXAMPLE 4A
(according to the invention)

EXAMPLE 4B

Viscosity measurements were carried out using a Haake VT550 viscometer equipped with an MV B Din cylindrical spindle, at 25° C.

The graph in the attached FIGURE shows that the viscosity of the formulation according to the invention (Example 4A), which contains "Tween 21" is markedly higher than the viscosity of the formulation containing "Tween 20", which is totally liquid (Example 4B).

What is claimed is:

1. A composition for washing keratin materials comprising, in a cosmetically acceptable aqueous medium containing at least one anionic detergent surfactant, at least one sorbitan ester of a saturated or unsaturated, linear or branched $C_8$–$C_{30}$ fatty acid, oxyethylenated with a number of moles of ethylene oxide of less than or equal to 10, wherein the weight ratio of anionic detergent surfactant to sorbitan ester ranges from 0.5 to 5.

2. A composition according to claim 1, comprising at least one $C_8$–$C_{20}$ fatty acid ester of sorbitan which is oxyethylenated with a number of moles of ethylene oxide of less than or equal to 10.

3. A composition according to claim 1, wherein the oxyethylenated sorbitan ester contains 3 to 8 mol of ethylene oxide.

4. A composition according to claim 1, wherein the sorbitan ester is selected from the group consisting of oxyethylenated sorbitan monolaurate (4EO), oxyethylenated sorbitan monostearate (4EO) and oxyethylenated sorbitan monooleate (5EO).

5. A composition according to claim 1, wherein the sorbitan ester is present in a proportion of from 0.5% to 20% relative to the weight of the composition.

6. A composition according to claim 5, wherein the sorbitan ester is present in a proportion of from 2% to 15% relative to the weight of the composition.

7. A composition according to claim 1, further comprising at least one detergent surfactant selected from the group consisting of a nonionic surfactant other than oxyethylenated $C_8$–$C_{30}$ fatty acid esters of sorbitan with a number of moles of ethylene oxide of less than or equal to 10, an amphoteric surfactant and a zwitterionic surfactant.

8. A composition according to claim 1, wherein the detergent surfactant is present in a proportion of between 1% and 50% by weight relative to the total weight of the composition.

9. A composition according to claim 8, wherein the detergent surfactant is present in a proportion of between 5% and 40% by weight relative to the total weight of the composition.

10. A composition according to claim 1, further comprising at least one cationic surfactant.

11. A composition according to claim 1, further comprising at least one silicone.

12. A composition according to claim 1, further comprising at least one polymer selected from the group consisting of a cationic polymer and an amphoteric polymer.

13. A composition according to claim 12, wherein said cationic polymer is selected from the group consisting of a cellulose ether derivative comprising at least one quaternary ammonium group and a polysaccharide.

14. A composition according to claim 13, wherein said polysaccharide is selected from the group consisting of a cationic guar gum, a cyclopolymer of methyldiallylammonium and a cyclopolymer of dimethyldiallylammonium.

15. A composition according to claim 1, further comprising at least one component selected from the group consisting of a viscosity regulator and a thickener.

16. A composition according to claim 15, wherein said viscosity regulator is at least one electrolyte and said thickener is at least one component selected from the group consisting of a cellulose derivative, a guar gum, a hydroxypropyl guar gum, a scleroglucan, a xanthan gum and an amphiphilic polymer comprising at least one fatty chain.

17. A composition according to claim 16, wherein said at least one electrolyte is sodium chloride.

18. A composition according to claim 1, further comprising at least one adjuvant selected from the group consisting of a fragrance, a preserving agent, a foam synergist, a sequestering agent, a foam stabilizer, a propellant, a dye, an antidandruff agent, a ceramide, a vitamin, a provitamin, an hydroxy acid, an acidifying agent, a basifying agent, a plant oil, a mineral oil, an animal oil, a synthetic oil, a fatty acid ester, a pseudoceramide and a nacreous agent.

19. A composition according to claim 18, wherein said synthetic oil is at least one of a polyisobutenes or a polydecene.

20. A method of at least one of reducing the eye-irritant potential of and of improving the thickening of a composition for washing a keratin material comprising a detergent surfactant, said method comprising combining at least one $C_8$–$C_{30}$ fatty acid ester of sorbitan having a number of moles of ethylene oxide of less than or equal to 10 to said composition.

21. A method according to claim 20, wherein said composition is a shampoo.

22. A process for washing a keratin material, comprising applying a composition of claim 1 to said material, followed by rinsing said material after said applying.

* * * * *